United States Patent [19]

Verschoof et al.

[11] Patent Number: 4,537,186

[45] Date of Patent: Aug. 27, 1985

[54] CONTRACEPTIVE DEVICE

[76] Inventors: Karel J. H. Verschoof, Staringstraat 31, 7514 DE Enschede; Jan W. Smit, Schumannlaan 31, 7522 KD Enschede, both of Netherlands

[21] Appl. No.: 528,865

[22] Filed: Sep. 2, 1983

Related U.S. Application Data

[63] Continuation of Ser. No. 378,821, May 17, 1982, abandoned, which is a continuation of Ser. No. 92,266, Nov. 8, 1979, abandoned.

[51] Int. Cl.³ .............................................. A61F 5/46
[52] U.S. Cl. ................................................... 128/130
[58] Field of Search .............. 128/127, 128, 130, 131, 128/1 R, 334 R, 334 C

[56] References Cited

U.S. PATENT DOCUMENTS

| 3,405,711 | 10/1968 | Ba Kunin | 128/130 |
| 3,441,018 | 4/1969 | Schneider | 128/130 |
| 3,680,542 | 5/1970 | Cimber | 128/1 R |
| 3,939,049 | 2/1976 | Ratner et al. | 204/159.13 |
| 3,975,350 | 8/1976 | Hudgin et al. | 3/1.91 |
| 4,056,496 | 11/1977 | Mancini et al. | 128/130 |
| 4,198,966 | 4/1980 | Kaivola | 128/130 |
| 4,353,363 | 10/1982 | Sope a Quesada | 128/130 |

FOREIGN PATENT DOCUMENTS 2328175 12/1974 Fed. Rep. of Germany .
1460077 1/1974 United Kingdom .

Primary Examiner—Stephen C. Pellegrino
Assistant Examiner—Harrie S. Samaras
Attorney, Agent, or Firm—Diller, Ramik & Wight

[57] ABSTRACT

Contraceptive device for intra uterine application in the oviducts having two enlargements 1, 2 connected by an oblong connection element 3 to a halter shape which enlargements remain fixed in the muscle tissues since the surface areas of the projections of these enlargements on a plane transverse to the longitudinal axis of the device are almost equal.

3 Claims, 6 Drawing Figures

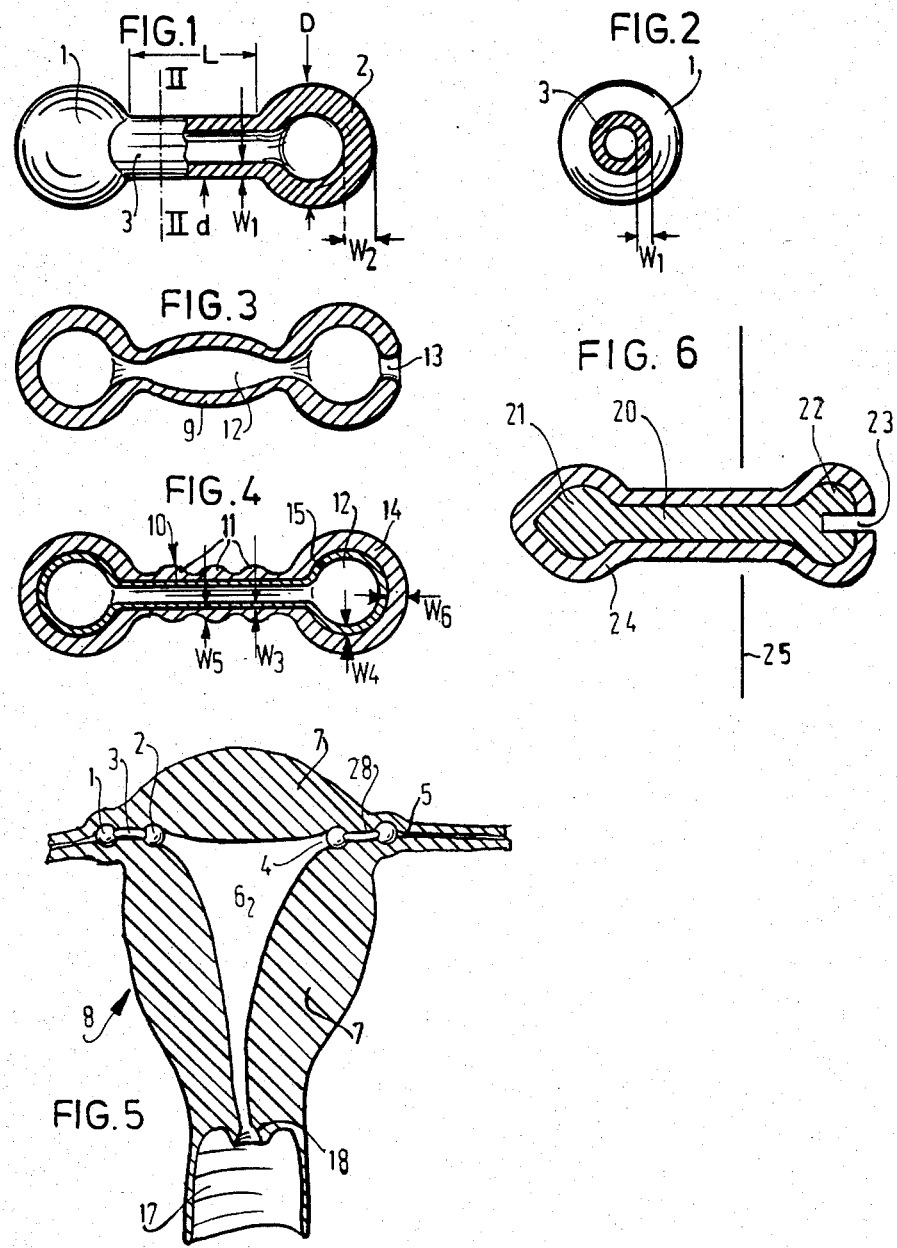

CONTRACEPTIVE DEVICE

This application is a continuation of application Ser. No. 378,821, filed 5/17/82, abandoned, which is a Rule 60 cont. Ser. No. 92,266 filed 11/8/79, abandoned.

The invention relates to a contraceptive device for intra uterine application having an oblong connection element connecting two separate enlargements having rounded shapes. A contraceptive device of this kind is disclosed in Dutch Patent Application No. 74 01380 and comprises an oblong elastic slightly curved element having club shaped enlargements at either end. The remote sides of these enlargements are semi spherical and the adjoining sides gradually merge into the connection element. The enlargements each are to be positioned in the opposite oviducts but cannot suitably be fixed therein. Moreover is the distance between the funnel shaped mouths of the opposite oviducts in the uterus not constant such that either an insufficient closure or an excessive pressure on the tissues surrounding the enlargements is the result. The changes in distance can be partly compensated by making the connection element, having a length of some centimeters, curved and of a flexible material, but this is not reliable.

Object of the invention is to provide an improved contraceptive device which can be reliably positioned and fixed in the oviducts since the enlargements and the oblong connection element are of a dumb-bell shape and the surface areas of the projections of these enlargements on a plane transverse to the longitudinal axis of the device are almost equal, and the enlargements abruptly merging into the connection element.

This contraceptive device is to be positioned such that one of the enlargements is just in the oviduct mouth and the other in the oviduct on the outside of the muscle tissue of the uterus.

For obtaining a good closure of the oviducts while preventing an appreciable irritation the enlargements having a diameter of from 2-6 mm, the sandwiched connection element being 2-14 mm long and having a thickness amounting 0.4:1 to 0.8:1 times the largest diameter of the enlargements is to be preferred. In order to follow temporary dilatation of the oviducts the enlargements preferably are at least partly made of rubber elastic material.

If the dilatations of the oviducts are prolonged these can be compensated by the contraceptive device provided at least part of it is having a circular layer of a material which can highly expand by water absorption. An example of such material is a hydrogel, particularly polyhema, that is to say poly(hydroxyethyl)methacrylate. Preferably the contraceptive device is at least partly hollow and open at one end only.

The axial fixation of the device will in an important degree be the result of the forces exerted by the muscle tissue of the uterus on the facing surfaces of the enlargements. The closure predominantly takes place at the largest diameter of the enlargements, but also by the pressure exerted by the muscle tissue of the uterus on the oblong connection element. This closure can be improved by providing the connection element with at least one circular rib, which of course has a smaller diameter than the enlargements.

The invention will be explained in connection with the drawing in which some preferred embodiments of the contraceptive devices and its use are depicted.

FIG. 1 shows a partly axial sectioned contraceptive device.

FIG. 2 shows a transverse section along the line II—II in FIG. 1.

FIGS. 3 and 4 show axial sections of modified embodiments of the device shown in FIG. 1.

FIG. 5 shows the use of the contraceptive device according to the invention.

FIG. 6 shows an axial section of a modified embodiment of the device shown in FIG. 1.

The contraceptive device or plug as shown in FIG. 1 is of generally dumb-bell shape and comprises two spherical enlargements or bulbous portions 1, 2 and a cylindrical oblong connection element 3. The device is entirely hollow. The wall thickness w 1 of the connection element and the wall thickness w 2 of the enlargements are dependent on the required elasticity of such parts.

In the depicted embodiment the ratio between the diameter D of the connection element 3 and the diameter d of the enlargements 1, 2 is about 0,5, but this ratio can be varied in dependence on the circumstances from 0.4:1 to 0.8:1. A smaller ratio will prevent a seal on the connection element and a larger ratio will increase the risk of axial rejection from the mouth of the oviducts if an unequal muscle contraction occurs. The values of these diameters d and D and of the length L of the connection element will be dependent on the anatomic shape of the mouths 28 of the oviducts in the uterus and on the diameters of the oviducts just outside the uterus wall.

In FIG. 5 the position of the contraceptive devices in the oviduct mouths 28 is shown: one of the enlargements still in the funnel shaped widened part 4 of the oviduct 5 in the uterus cavity and the other enlargement just outside the muscle tissue 7 of the uterus 8 in the oviduct. The several dimensions of the contraceptive device, particularly the length L of the connection element 3 have to be selected dependent on the anatomic data, in order that a suitable closure on all parts of the contraceptive device is obtained. The closure in the mouths 28 may be improved by providing the connection element with at least one circular rib as depicted in FIGS. 3 and 4. In FIG. 3 the oblong element 9 is elliptic in longitudinal section, while in FIG. 4 the oblong element 10 has three peripheral ribs 11 with rounded shapes for preventing tissue irritation.

Just like the embodiment as shown in FIG. 1 that of FIG. 3 is hollow, although in the latter case the internal cavity 12 debouches at one end through an opening 13 to the atmosphere enabling measuring instruments to be accomodated in the cavity and applying tools to grip in it.

The embodiment of FIG. 4 is also different from that of FIG. 1 in that a layered construction is used: the outer layer 14 may be a tissue friendly material, which property is not required for the material of the inner layer 15, which material may be chosen for its mechanical properties such as a certain elasticity.

The contraceptive device preferably is of at least an outer material which can highly increase in volume by water absorption, such as a hydrogel, offering the advantage that on dilatation of the cavity accomodating the device diameter increase will result by water absorption, so that the closure is safeguarded. By pressure increase after diameter decrease that material can loose water so that after a certain time the pressure exerted by the device on the surrounding tissues has an acceptable value again. Adapting the pressure is possible by a suitable selection of the materials of both layers and a selection of the wall thickness w 3 and w 4 of the inner layer 15 of the connection element and the enlargements respectively and the wall thickness w 5 and w 6 of the outer layer 14 of these parts.

In FIG. 6 an axial section through a modified embodiment is shown, comprising an asymmetric core 20 made of copper and being rotary symmetric around its longitudinal axis. The core comprises a connection element 21 and two enlargements at its two ends. The one enlargement 21 is slightly pointed at its free end for easier application, the other enlargement 22 being flattened at its free end and having an axial bore 23 for applying tools to grip in.

The core is all round coated with a layer of polyhema 24. Despite the asymmetric shape this embodiment satisfies the requirement that the surface areas of the projections of both enlargements on a plane 25 transverse to the longitudinal direction have to be equal.

It may be evident that the contraceptive devices shown in FIGS. 3 and 6 are positioned with the opening 13, 23 respectively towards the uterus cavity 6.

We claim:

1. A contraceptive device comprising a body adapted to block an oviduct passage through a user's uterine muscle tissue, said body having a first means for effecting closure of the oviduct passage by forcibly seating against the uterine muscle tissue at and around the mouth defined at the opening of the oviduct passage into the uterine cavity, an elongate connection means connected with said first means for extending therefrom through said mouth of the oviduct passage, and a second means connected with said elongate connection means for effecting closure of the oviduct passage opening where the user's Fallopian tube connects with the oviduct passage by forcibly seating against the uterine muscle tissue at and around such oviduct passage opening, said first and second means being of bulbous form abruptly enlarged with respect to said connection means to present opposed surface portions, said elongate connection means being of a length in the range of about 2–14 mm determined from anatomic data of the user which assures that said opposed surface portions are forcibly seated against the uterine muscle tissue to effect their closures of the oviduct passage predominantly at the largest diameters of the bulbous portions respectively at said mouth of the oviduct passage and at said opening of the oviduct passage where the Fallopian tube connects with the oviduct passage, said connection means being of generally cylindrical form and of sufficient diameter as determined from anatomical data of the user so as to be completely surrounded and gripped by such muscle tissue to effect further closure of said passage, said opposed surface portions having substantially the same area when projected onto a plane transverse to the longitudinal axis of said body so that oppositely directed and substantially balancing forces are exerted thereon by the uterine muscle tissue to effect axial fixation of the device, and said elongate connection means having a diameter in the range of about 2–6 mm and which, with respect to the diameter of each of said bulbous portions is in the range of 0.4:1 to 0.8:1 so that both gripping of the connection means by the uterine muscle tissue and axial fixation are preserved.

2. A contraceptive device as defined in claim 1 including means forming at least the outer surface of said body for swelling and contracting by absorbing and losing water in dependence upon pressure exerted by body tissues whereby to accommodate for normal contractions and dilations of such body tissues.

3. A contraceptive device as defined in claim 1 or 2 wherein said body is hollow.

* * * * *